(12) United States Patent
Utermohlen et al.

(10) Patent No.: US 6,656,685 B2
(45) Date of Patent: Dec. 2, 2003

(54) HYBRIDIZATION BUFFERS USING LOW MOLECULAR WEIGHT DEXTRAN SULFATE AND METHODS FOR THEIR USE

(75) Inventors: Joseph Utermohlen, Tucson, AZ (US); Catherine Wolf, Eckbolsheim (FR); Kimberly Christensen, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 09/772,123

(22) Filed: Jan. 29, 2001

(65) Prior Publication Data

US 2002/0102554 A1 Aug. 1, 2002

(51) Int. Cl.$^7$ .......................... C12Q 1/68; C12P 19/34; C08B 37/02; A01N 43/04; A61K 31/715
(52) U.S. Cl. .......................... 435/6; 435/91.2; 435/103; 514/59; 514/54; 536/51
(58) Field of Search .......................... 435/6, 103, 91.2; 514/59, 54; 536/51

(56) References Cited

U.S. PATENT DOCUMENTS

| | | | | |
|---|---|---|---|---|
| 4,302,204 A | * | 11/1981 | Wahl et al. | .................... 23/230 |
| 4,689,294 A | | 8/1987 | Boguslawski et al. | |
| 4,886,741 A | * | 12/1989 | Schwartz et al. | .............. 435/6 |
| 5,750,340 A | | 5/1998 | Kim et al. | |
| 5,985,549 A | | 11/1999 | Singer et al. | |

FOREIGN PATENT DOCUMENTS

| | | |
|---|---|---|
| EP | 0508568 A2 | 10/1992 |
| WO | WO89/05357 | 6/1989 |

OTHER PUBLICATIONS

Amasino, "Acceleration of Nucleic Acid Hybridization Rate by Polyethylene Glycol," Analytical Biochemistry, vol. 152 (No. 2), p. 304–307, (Feb. 1, 1986).
Barr, et al, "Application of a Subtraction Hybridization Technique Involving Photoactivatable Biotin and Organic Extraction to Solution Hybridization Analysis of Genomic DNA," Analytical Biochemistry, vol. 186 (No. 2), p. 369–373, (May 1, 1990).
Flemming, et al, "Optimization of Non–Isotopic In Situ Hybridization on Formalin–Fixed, Paraffin–Embedded Material Using Digoxigenin–Labelled Probes and Transgenic Tissues," Journal of Pathology, vol. 167 (No. 1), p. 9–17, (Feb. 10, 1992).
Gingeras, et al, "Hybridization Properties of Immobilized Nucleic Acid," Nucleic Acids Research, IRL Press Limited (Oxford, England), vol. 15 (No. 13), p. 5373–5390, (Jul. 10, 1987).
Harper, et al, "Localization of Single Copy DNA Sequences on G–Banded Human Chromosomes by in situ Hybridization," Chromosoma, Springer–Verlag, vol. 83 (No. 3), p. 431–439, (1981).
Lederman, et al, "The Rate of Nucleic Acid Annealing to Cytological Preparations is Increased in the Presence of Dextran Sulfate," Analytical Biochemistry, vol. 117 (No. 1), p. 158–163, (Oct. 1981).
Maki, et al, "Nonradioactive in Situ Hybridization Histochemistry in Leukemic and Nonleukemic Culture," Biotechnical and Histochemistry, vol. 72 (No. 1), p. 38–44, (Jan. 1997).
Meinkoth, et al, "Hybridization of Nucleic Acids Immobilized on Solid Supports," Analytical Biochemistry, vol. 138 (No. 2), p. 267–284, (May 1, 1984).
Van Gijlswijk, et al, "Improved Localization of Fluorescent Tyramides for Fluorescence in Situ Hybridization Using Dextran Sulfate," Journal of Histochemistry and Cytochemistry, vol. 44 (No. 4), p. 389–392, (Apr. 3, 1996).
Wahl, et al, "Efficient Transfer of Large DNA Fragments from Agarose Gels to Diazobenzyloxymethyl–paper and Rapid Hybridization by Using Dextran Sulfate," Proceeding of the National Academy of Sciences USA, vol. 76 (No. 8), p. 3683–3687, (Aug. 1979).

* cited by examiner

*Primary Examiner*—Ethan Whisenant
*Assistant Examiner*—Joyce Tung
(74) *Attorney, Agent, or Firm*—Huw R. Jones

(57) ABSTRACT

The invention is directed to an improvement in automated tissue staining system having evaporation inhibitor liquid covering the polynucleotide hybridization buffer-covered tissue on a slide, wherein the improvement comprises a polynucleotide hybridization buffer for in situ hybridization comprising a low molecular weight dextran sulfate having a molecular weight range from about 8,000 to about 16,000.

4 Claims, 13 Drawing Sheets

(13 of 13 Drawing Sheet(s) Filed in Color)

HYBRIDIZATION BUFFERS USING LOW MOLECULAR WEIGHT DEXTRAN SULFATE AND METHODS FOR THEIR USE

BACKGROUND

1. Field of the Invention

This invention relates to methods for using volume exclusion agents to enhance in situ hybridization between polynucleotide probes and their target polynucleotides, particularly in an automated testing environment. In one aspect, the invention specifically relates to the use of volume exclusion agents to facilitate assay and diagnostic procedures for the detection of DNA and RNA sequences, particularly human papillomavirus (HPV), Epstein Bar virus (EBV), human immunoglobulin light chain mRNA (Kappa and Lambda sequences), and Her-2/neu gene.

2. Description of Related Art

Hybridization is a general technique in which the complementary strands of deoxyribonucleic acid (hereinafter "DNA") molecules, ribonucleic acid (hereinafter "RNA") molecules, and combinations of DNA and RNA are separated into single strands and then allowed to renature or reanneal into base-paired double helices. At least three major classes of hybridization are conventionally known and used: solution hybridization which disrupts the individual cells and extracts the internal nucleic acids into solution prior to hybridization; filter or blot hybridization which transfers extracted DNA (or RNA) fragments from agarose gels to filters or blotters such as cellulose nitrate or nylon for subsequent hybridization with radioactive DNA or (RNA) and then detection of hybridization by radioautography or fluorography; and in situ hybridization ("ISH") which makes possible the detection and localization of specific nucleic acid or polynucleotide sequences directly within a structurally intact cell or cellular component where extraction of nucleic acids from the cell is undesirable. Although each of these respective hybridization techniques often employ cells, tissues, and certain reagents in common, each technique is generally viewed and accepted within this art as different and completely distinguishable from any other.

In situ hybridization is a technique which yields both molecular and morphological information about intact individual cells and cellular parts. Rather than requiring the investigator to laboriously extract DNA and/or RNA from a heterogeneous cell population, the technique permits detection of DNA and RNA in-situ within the cellular morphology and allows the investigator to identify those particular cells or cell parts which contain specific DNA or RNA sequences of interest. This technique also allows one to determine simultaneously the biochemical and/or morphological characteristics of these cells. For this reason, the in situ hybridization methodology has direct application for many areas of biomedical and clinical research including developmental biology, cell biology, genetics, clinical diagnosis, and pathological evaluation.

Despite the potential of in-situ hybridization as a molecular analytical technique, the development of effective protocols and procedures has been largely haphazard and disjointed. Since first described in 1969 by Gall et al., P.N.A.S. U.S.A., 63:378–383 (1969); Methods in Enzymol., 38:370–380 (1971), the in situ hybridization approach has been directed towards two different morphological situations: the localization of specific nucleic acid sequences of interest in the cytoplasm of a cell; and the identification of specific nucleic acids within the nucleus and/or chromosomes of a cell.

Much of the research related to hybridization between target and probe polynucleotides for assay and diagnostic purposes has been directed toward optimizing rates of hybridization. In situ hybridization is particularly problematic due to the inability of the probes to readily enter into the nucleus or cytoplasm in which their target polynucleotides are located. To solve this problem, researchers have attempted, inter alia, to reduce the size of the probe and to alter cell fixation procedures to facilitate entry of the probe into the cytoplasm or nucleus, see generally Singer, R. H., et al., "Optimization of In Situ Hybridization Using Isotopic and Non-Isotopic Detection Methods," Biotechniques 4(3):230–250, 1986, and Haase, A., et al., "Detection of Viral Nucleic Acids by In Situ Hybridization," Methods in Virology, Vol. VII, pp. 189–226, (1984). Amasino, R. M., "Acceleration of Nucleic Acid Rate by Polyethylene Glycol," Anal. Biochem., 152:304–307 (1986). It has been reported that the effect of dextran sulfate, the most commonly used exclusion agent, was most pronounced in mixed phase hybridizations where the probes exceeded 250 nucleotides. Further, it has been reported that as the probe size decreases, so would the enhancing effect of dextran sulfate on the rate of hybridization, with no effect observed for oligonucleotides of 14 bases. Meinkoth J. and Wahl J., "Hybridization of Nucleic Acids Immobilized on Solid Supports" (Review), Anal. Biochem., 138:267–284 at 268 (1984). The use of volume exclusion to enhance in situ hybridization has also been reported. It was reported that an average length of 400 nucleotides is optimal for hybridization in situ in the presence of dextran sulfate. Hasse, A., supra. at 205.

Early references that disclose the use of dextran sulfate as a volume exclusion agent include Wahl, G. M., et al., "Efficient transfer of large DNA fragments from agarose gels to diazobezyloxymethyl-paper and rapid hybridization using dextran sulfate," PNAS 76: 3683 (1979); and Ledermann, L. L., et al., "The rate of nucleic acid annealing to cytological preparations is increased by the presence of dextran sulfate," Anal. Biochem., 117(1): 158–163 (1981).

The in situ localization of HPV DNA using long biotinylated probes in the presence of dextran sulfate has also been reported by Beckmann, P. M., et al.; "Detection and Localization of Human Papillomavirus DNA in Human Genital Condylomas by In Situ Hybridization with Biotinylated Probes," J. Med. Virol., 16:265–273 (1985); Milde K., Loning, T., "Detection of Papillomavirus DNA in Oral Papillomas and Carcinomas: Application of In Situ Hybridization with Biotinylated HPV 16 probes," J. Oral Pathol., 15:292–296 (1986); and McDougall, J. K., et al., "Methods for Diagnosing Papillomavirus Infection," in Papillomaviruses, Wiley, Chicester (CIBA Foundation Symposium 120), pp. 86–103 (1986).

U.S. Pat. No. 5,985,549 (Singer, et al.) demonstrates the use of a dextran sulfate hybridization buffer containing formamide (deionized); dextran sulfate (10%); human DNA or salmon sperm DNA (100 ug/ml); human tRNA (100 ug/ml); and vanadyl sulfate (10 uM) for ISH. The molecular weight of dextran sulfate was not disclosed, and it is assumed that 500,000 average molecular weight was obtained.

U.S. Pat. No. 5,750,340 (Kim, I., et al.) disclose a hybridization solution for performing ISH, the solution consisting essentially of 8–12% dextran sulfate, 10–30% formamide, and a salt. No source for the dextran sulfate, or molecular weight, is specified.

U.S. Pat. No. 5,116,727 (Brigatti) discloses hybridization buffers that contain anionic heteropolysaccharides (e.g.

chondroitin A sulfate) as useful volume exclusion agents for accelerating hybridization reactions. Chondroitin A sulfate hybridization buffers were of low viscosity which was a useful property for capillary gap slides and their use in the automated processing of in situ hybridization reactions. Brigatti teaches that the low viscosity of this buffer is due to the volume exclusion agent having an anionic heteropolysaccharide structure; this was compared to anionic polysaccharides like dextran sulfate. Brigatti further discloses that anionic homopolysaccharides like dextran sulfate polymers produce buffers of substantially greater viscosity based on the their monomeric structure. This high viscosity makes such hybridization buffers non-ideal for capillary gap technology since high viscosity inhibits both probe diffusing in and out from target and during wash steps to wash away excess probe. Brigatti further teaches that increasing the concentration of dextran sulfate also increases the viscosity and thus inhibits the hybridization process.

U.S. Pat. No. 4,886,741 (Schwartz et al.) describe the use of dextran sulfate, sodium salt, for use as a volume exclusion agent for ISH. The average molecular weight is not described, but by reference to the source (Sigma Chemical, Products for Life Sciences, St. Louis, Mo.) it has an average molecular weight of 500,000. Schwartz et al. also disclose that dextran sulfate is typically used at a concentration of about 5–10% (w/v).

U.S. Pat. No. 4,302,204 (Wahl, G., et al.), describes the use of dextran sulfate polymers for hybridization buffers used for in vitro blot hybridization. In this patent however, the preferred hybridization buffer contained dextran sulfate of 500,000 MW. No examples were presented that used low molecular weight dextran sulfate nor was an in situ reaction presented or claimed.

In the field of nucleic acid hybridization, the need for rapid assay tests for the accurate and reproducible detection of nucleic acids has been a long standing problem. Any procedures that demonstrate a tendency to accelerate the typically multi-hour long processes are of value, especially for hybridization assays to be conducted by clinical laboratories.

SUMMARY OF THE INVENTION

This invention demonstrates that lower molecular weight dextran sulfate is also an effective volume exclusion agent for hybridization reactions. The hybridization buffers of this invention utilize smaller polymers of dextran sulfate, and thus are of a lower viscosity than conventional hybridization buffers that use higher molecular weight dextran sulfate polymers as volume exclusion agents. The lower viscosity of these low molecular weight dextran sulfate polymer buffers makes them useful for automated hybridization processes as in dispensing, automated flow, and mixing on slide.

The invention is directed to an improvement in automated tissue staining system having evaporation inhibitor liquid covering the polynucleotide hybridization buffer-covered tissue on a slide, wherein the improvement comprises a polynucleotide hybridization buffer for in situ hybridization comprising a low molecular weight dextran sulfate having a molecular weight range from about 8,000 to about 16,000.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DESCRIPTION OF THE PREFERRED EMBODIMENTS

Figure 1A:
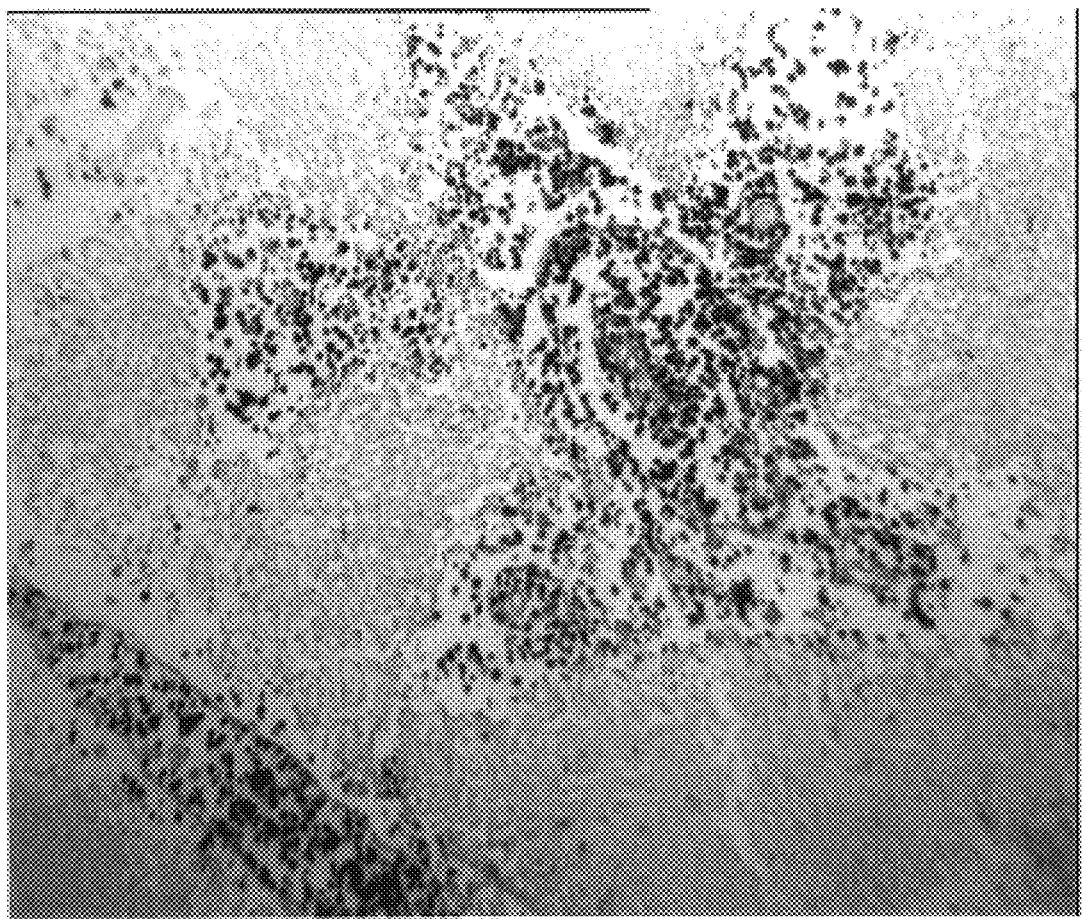
FIGS. 1A and 1B are color photographs of human spleen tissue samples hybridized with a DNA probe collection consisting of probes possessing target gene-specific domains corresponding to EBV EBER 1 and 2 nuclear RNA, wherein the tissue sample was not treated with ribonuclease A prior to in situ hybridization (A), or was treated with ribonuclease A prior to in situ hybridization (B).

The inventors have demonstrated herein that low molecular weight dextran sulfate polymers of approximately 10,000 MW (molecular weight) are effective volume exclusion agents for hybridization reactions between DNA:DNA, DNA:RNA, and RNA:RNA. Buffers comprising dextran sulfate within the range of 10,000 MW performed well for both nick translated labeled probes, oligonucletide DNA probes, and in vitro transcribed labeled RNA probes. The target type of nucleic acids were chromosomal (interphase cells), nuclear RNA (EBER), and mRNA targets. Both calorimetric ISH and FISH probes were tested with these buffers. The buffers worked with paraffin embedded formalin-fixed tissues and cell line, sections, cytospin cell preparations, and ThinPrep™ (a liquid-based preparation) cell preparations. Surprisingly, these buffers behaved as well or better than comparable buffers made using standard 500,000–2,000,000 MW dextran sulfate polymer.

Generally, volume exclusion agents are added to hybridization buffers to accelerate the re-association of complementary DNA. The increase in reassociation kinetics associated with conventional dextran sulfate polymers (500,000 to 2,000,000 MW) are in the range of 8 to 15 times when compared to buffers lacking this volume exclusion agent (Wetmur, J. G., 1975, Biopolymers 14:2517–2524; Wahl and Stark, U.S. Pat. No. 4,302,204). The preferred concentration (weight to volume) for dextran sulfate polymers (500,000–2,000,000 MW) is between 5% to 10%. The key work for describing the acceleration affect of dextran sulfate polymers as volume exclusion was Wetmur, supra. The relative molecular weight of dextran sulfates disclosed were 500,000 and 2,000,000 MW. The effectiveness of low molecular weight dextran sulfate polymers at as volume exclusion agents were not tested.

The inventors addressed several fundamental issues when they undertook to develop these low-viscosity ISH hybridization buffers, such as:

whether low molecular weight (8,000 to 15,000) range polymer dextran sulfate would be an effective volume exclusion agent for hybridization buffers;

whether buffers with these smaller polymers would be effective in automated in situ hybridization reactions using the Ventana Medical Systems, Inc. coverslip technology;

whether higher viscosity was a property necessary for dextran sulfate buffers to be effective for hybridization;

whether these lower molecular weight polymers would function with oligonucleotide probes because Schwartz (U.S. Pat. No. 4,886,741) example's were of buffers with high molecular weight dextran sulfate polymers. The inference being that smaller polymers may not be effective;

whether these buffers would mix with other solutions on a slide to form an effective hybridization solution;

whether smaller size and greater solubility of volume exclusion agents impacts rinsing performance in removing probe and hybridization buffer during post hybridization washes, hence reducing aberrant signal on sample tissues; and whether formamide in the buffer would be incompatible. The effect of formamide in accelerating hybridization is not well understood. Most studies suggest that formamide actually reduces the hybridization reaction (J. R. Hutton, "Renaturation kinetics and thermal stability of DNA in aqueous solutions of formamide and urea," Nucelic Acid. Res. 4(10):3537–3555, October 1977) at concentrations greater than 25% by volume. The properties of higher molecular weight dextran sulfate polymers as volume exclusion agents may have been due to the property of increased viscosity, or its higher molecular weight may have been a synergistic result with formamide or alditols. The polymers described by Brigatti (U.S. Pat. No. 5,116,727, supra) were 10-fold smaller than dextran sulfate 500,000, though these were taught to be distinct from dextran sulfate since they were heteropolysaccharide polymers, a property unique to Chondroitin A sulfate volume exclusion agents. So whether the smaller dextran sulfate polymers were effective volume exclusion agents was not defined nor understood at the beginning of these studies.

For automated processes, a hybridization buffer of low viscosity is desired for hybridization reactions. Automated in situ hybridization using Ventana Medical Systems' DISCOVERY™, NexES® or BENCHMARK™ instruments utilizes a LIQUID COVERSLIP™ to prevent evaporative loss of reagent during the reaction. The compatibility of hybridization buffer with low molecular weight dextran sulfate with Ventana's liquid coverslip system was not known. Compatibility of buffer and a wide range of probe types on Ventana's slide staining systems was an unknown prior to these studies. These buffers have been found useful with synthetic oligo-nucleotide probes, nick translated DNA probes from plasmids or cosmid origin, and in vitro synthesized RNA.

Automated slide processing on the Ventana DISCOVERY™ automated ISH stainer was the test system used with these buffers. This staining system relies on mixing through counter-rotation of the Liquid Coverslip with air jets to stimulate the mixing of reagent on the slide and the full distribution of reagents across the surface of the slide. The Ventana process works best if the reagents are of viscosities similar to or less than water. Reagents of high viscosities are not easily adapted to the DISCOVERY system. Many of the conventional hybridization buffers that use high molecular weight anionic homopolymers of dextran sulfate are not effective on this staining system.

To the best of the inventor's knowledge, the utility of low molecular weight polymers has not been fully explored in the hybridization literature as to their effectiveness in driving nucleic acid re-association. The polymeric size of dextran sulfate that has been demonstrated as effective in driving nucleic acid reassociation is in the range of 500,000 to 2,000,000 MW. However, the inventors have found that much lower MW dextrans having lower viscosities can be used, with the additive result that low molecular weight, low-viscosity dextran sulfate based hybridization buffers can be used in the small-volume environment of an automated instrument. This was a surprising result because at least one commentator has observed that homopolymers such as dextran sulfate will be most effective at high average molecular weights as volume exclusion agents (see Brigatti, U.S. Pat. No. 5,516,727, discussed supra). The viscosity and solubility characteristics of any polymer in solution (at a given concentration) is a function of its Stokes radius, or the molecular volume of the polymer. Thus larger polymers have a lower solubility and induce solutions of greater viscosity for any two polymers of the same monomeric unit.

The greater solubility of smaller average molecular weight dextran sulfate polymers allows the formulation of hybridization buffers with dextran sulfate polymers at concentrations equal to or greater than 10% in the presence of formamide concentrations ranging from 5% to 80%. This allows for solutions to be formulated at 2× stock solutions. Mixing hybridization buffers from 2× stock solution can be mixed on the slide with aqueous solutions to make the hybridization buffer with optimal concentrations for all constituents.

Compositions of Hybridization Buffers with Low Molecular Weight Dextran Sulfate Polymers Buffer A:

20% wt/vol dextran sulfate at 10K average molecular weight

50% vol/vol formamide 10 mM Tris (15:85 of Tris-HCl:Tris-OH)

5 mM EDTA 300 mM NaCl 30 mM trisodium citrate (Na3C6H5O 7)

0.05% Brij-35 pH=7.3

Buffer A can be used directly with no further dilution, in an automated format using the manually-applied protocol for ISH. This solution can also be used via an automated protocol as an approximately 2× concentrated solution, that is dispensed into an equal volume of 2× SSC-Triton X100 for most automated processes. 1× SSC comprises 0.15M NaCl; 0.015 M trisodium citrate. The resultant on-slide hybridization solution is 50% of the concentration of Buffer A with the exception of NaCl and trisodium citrate concentrations, which remain the same.

The concentration of pH can range from 6–8, however, the most preferred is 7.3.

Modifications to the base low-molecular weight buffer are useful for specific vapplications, for instance, in the hybridization of DNA or RNA probes to mRNA (Buffer B):
20% wt/vol dextran sulfate at 10K average molecular weight
80% vol/vol formamide
2× SSPE
0.05% Brij-35

1× SSPE is a stock solution comprising the following: 150 mM NaCl, 8 mM Na2HPO4, 2 mM NaH2PO4, 1 mM EDTA, in water. Buffer B can be used via automated protocol as an approximately 2 times concentration solution, that is dispensed into an equal volume of 2× SSPE, 0.025% Triton-X100, and 0.025% Brij-35 for most automated processes. The resultant hybridization solution would be: 10% wt/vol dextran sulfate at 10K average molecular weight, 40% vol/vol formamide, 2× SSPE, and 0.025% Brij-35. The preferred range of concentration of formamide is from about 20% to about 80%, a more preferred concentration is from about 40% to 80%, and the most preferred concentration is 80% (40% on the slide). The preferred range of concentration of SSPE is from about 2–4×, while the most preferred concentration is 2× SSPE.

Another variant of the low molecular weight dextran sulfate hybridization buffer of Buffer A is used preferably for automatically hybridizing "DNA chips" built on glass microscope slides which are typically sold by companies such as Incyte and ClonTech. The composition of the buffer (Buffer C) is: 6× SSPE, 20% dextran sulfate (10K MW), and 10% formamide. Buffer C is typically run on the instrument in a 1:1 dilution with 2× SSPE, 0.0125% Triton-X100, and 0.025% Brij-35. One of the great advantages of Buffer C is that is that it is formulated to maximize spreadability of the buffer on the slide surface, thus covering all of the available probe arrays. A preferred concentration of SSPE ranges from 2–8×, while more preferred is 3–7× and most preferred is 6×. The preferred concentration range of formamide is 0–20%, more preferred is from 5–15%, and most preferred is 10%.

The low-molecular weight dextran sulfate used herein was sourced from Sigma Chemical. It is sold by Sigma as having an average molecular weight of approximately 10,000. However, the mean molecular weight (that is by analysis the molecular weight of a minimum of 75% of the total population of dextran sulfate polymers) for three lots of Sigma product Dextran Sulfate (catalogue number D-6924), was, for lot numbers 49H0530, 100K1379, and 070K0848, 12,750 MW, 13,360 MW, and 13,360 MW, respectively. The range of the molecular weight for this material is within two standard deviations (8,000 to 16,000 MW). Therefor, the term "low-molecular weight dextran sulfate" has some variability associated with it, since it is a polymer that is not well-controlled in terms of its average size.

The invention is also directed to a method of automatically hybridizing a nucleic acid probe to a target, comprising the steps of preparing a section of tissue or cells to be examined; hybridizing the tissue section or cellular preparation with a nucleic acid probe composition in the presence of low molecular weight dextran sulfate wherein said probe composition contains at least one sequence complementary to a coding region of the target; removing unhybridized probe from said tissue section or cellular preparation; and detecting the hybridized probe-target combination.

Automatic hybridization is the term used to describe the hybridization of a probe to a target by an automated instrument, such as those sold by Ventana Medical Systems. These include the models ES®, NexES®, DISCOVERY™, and BENCHMARK™. Preparation of the tissue or cell sample is manual, as is loading of the slides onto the system. The hybridization process is carried out by the instrument using a pre-loaded protocol that is adapted specially for use on the automated stainer. One of ordinary skill is fully capable of operating an automated staining instrument to perform automated hybridization reactions, once trained for the specifics of the instruments. Similarly, nucleic acid probe compositions are well-known in the art, and available commercially from a number of sources, including Ventana, Novocastra, Zymed, Vysis, and Enzo. The removal of unhybridized probe from the sample is performed by the automated stainer instrument by a pre-programmed washing function which is a a part of the protocol. The detection function is similarly a part of the protocol. Standard detection reagents are used, as sold by Ventana for use on its instrument platforms. The categories of labels used to detect hybridized probes include fluorophres, haptens, and chromogens. One of ordinary skill is aware of specific labels and their strengths and weaknesses in a particular detection setting. Primary detection schemes may be used where the probe is directly labeled and visualized with a fluorophore such as fluoroscein or Texas Red (available from Molecular Probes, Eugene, Oreg.) or an antibody-mediated secondary detection scheme may be used.

The invention may be used with either a tissue sample preparation such as a tissue sample sectioned from a paraffin-embedded tissue block using a microtome, or a cellular composition made from a liquid-based prep such as the Thin Prep™, available from Cytyc, Inc., Boxborough, Mass. A liquid-based preparation is simply a microscope slide having a mono-layer of cells spread evenly on its surface. The cells are collected in a collection vial and suspended in a medium that preserves them for later analysis. An aliquot of the suspension is filtered through a filter, and the filter is then imprinted upon the slide, adhering a thin layer of cells tot he glass surface of the slide.

Blocking DNA may be used in conjunction with the nucleic acid probes to reduce the background signal inherent whenever one is probing chromosomal DNA. U.S. Pat. No. 5,5447,841 (Gray, J., et al.) describe the method generally, which is hereby incorporated by reference.

The preferred embodiments of the hybridization buffers of the present invention are best understood by referring to the following Examples. The Examples, which follow, are illustrative of specific embodiments of the invention, and various uses thereof. They are set forth for explanatory purposes only, and are not to be taken as limiting the invention.

EXAMPLES

A. General Methods

Samples for ISH analysis were prepared by cutting formalin-fixed and paraffin-embedded cells or tissue samples into 4 $\mu$m sections and placing the sections onto a standard microscope glass slide. Subsequent processing and ISH of samples was carried out in an automated device, such as the DISCOVERY™ Automated ISH/IHC Stainer (Ventana Medical Systems, Inc., Tucson, Ariz.) described in co-owned and co-pending U.S. patent application Ser. Nos.

60/076,198 and 09/259,240, both incorporated herein by reference. To remove paraffin from the samples, the slides were immersed in an aqueous solution, heated for approximately 20 minutes, and then rinsed. The automated deparaffinization procedure is more fully described in U.S. Ser. Nos. 60/099,018, and 09/259,240 both incorporated herein by reference. The samples were then treated with Protease 1 and the slides were heated to 85° C. (for hybridization to RNA target genes) or 90–95° C. (for hybridization to DNA target genes) for 4 to 10 minutes.

Hybridization reactions were typically performed in a hybridization buffer consisting of a dilution of Buffer A into 2× SSC-Triton-X100, at a 1:1 ratio, and between 25 to 125 ng/mL of each individual probe molecule. ISH reactions were performed at between 37° C. to 54° C. For ISH using the oligonucleotide probes, as described in U.S. Provisional patent application 60/233,177, filed Sep. 15, 2000, incorporated by reference herein, hybridization reactions were carried out for 1 hr at 47° C. (except for the poly d(T) probe, wherein the hybridization reaction was optimally carried out at 37° C. for 1 hr).

The hybridization of fluorescein-labeled probes to a particular target gene in the sample was detected by using a sequential series of binding proteins, i.e., secondary antibody detection. However, it is equally possible to use direct detection when visualizing the bound probes. In secondary detection, first, an anti-fluorescein mouse monoclonal antibody directed against the fluorescein hapten bound to probe molecule was added to the sample. Next, a biotin-labeled polyclonal goat antibody directed against the mouse antibody was added to the sample. Finally, hybridization reactions were colormetrically detected using a 5-bromo-4-chloro-3-indolyl phosphate/nitroblue tetrazolium (BCIP/NBT) substrate. This technique, termed "secondary antibody detection," is routine for one of skill in the art. Primary and secondary antibodies are available from numerous suppliers, including Ventana Medical Systems, Tucson, Ariz., which are optimized for use on the Ventana autostaining systems (ES®, NexES®, DISCOVERY™, and BENCHMARK™.)

B. Examples

Example 1

In Situ Hybridization Using Buffer A in Comparision with Standard Dextran Sulfate Buffer A cocktail of two probes complimentary to the Alu human repetative sequence was used to evaluate the effectiveness of the lower molecular weight dextran sulfate as a viable volume exclusion agent for hybridization reactions. The two Alu probes used for the experiment to compare hybridization buffers containing low molecular weight dextran sulfate was a cocktail of two oligonucleotides, each with 3 fluorescein haptens attached per probe. These probes were dissolved at a combined concentration of 500 ng/mL. The two hybridization buffers are Buffer A, and a standard dextran sulfate buffer (500,000–2,000,000 mol. weight) buffer of 10% (wt/vol) dextran sulfate, 50% (vol/vol) formamide, 2× SSC, and 0.05% Brij-35, at a final pH of 7.3.

The hybridization was performed with a DISCOVERY™ instrument using the automated dispense protocol for probe and all other reagents. The sample was a paraffin-embedded cell line, Oncor INFORM™ Her-2/neu Control Slides, Cat. No. S8100, Level 1, available from Ventana Medical Systems, Inc., Tucson, Ariz. All slides were processed by removing paraffin by an automated aqueous deparaffinization method (see co-pending international patent application number PCT/US99/20353, incorporated herein by reference) followed by treatment with Ventana Protease 1 for 8 minutes at 50 degrees C. at a 1:2.7 dilution with Ventana's APK buffer. The sample cells were then equilibrated with 2× SSC (Ventana 2× SSC) then rinsed to remove all but a residual volume of approximately 100 μL on the slide. The probe and hybridization buffer at a 2× concentration were dispensed (100 μl) onto the slide and mixed with the residual volume of 2× SSC using air-jet mixing. After mixing, the slide was heated to 85C. within a 10 minute step, then cooled to 37C. for a 1 hour hybridization reaction. Standard 2× SSC at 37C. washes followed the hybridization for removing excess probe and probe non-specifically bound to DNA. Detection of the hybridized probe to Alu sequences carried out by secondary antibody detection via the binding of an anti-fluorescein, mouse antibody to fluorescein haptens attached to the probe followed by Ventana Enhanced Alkaline Phosphatase Blue Detection (Ventana cat# 760-061) chemistry. Unless otherwise indicated, all reagents were obtained from Ventana Medical Systems, Inc., Tucson, Ariz. and all of these reactions on the slide were performed under a film of LIQUID COVERSLIP™, to prevent evaporative loss of water during processing.

The results (observed colormetrically) were that the hybridization buffer containing the 20% concentration dextran sulfate of low molecular weight was more effective and more efficient in Ventana Medical Systems, Inc. staining automation. The reaction based on the low molecular weight dextran sulfate-containing buffer yielded a strong, intense signal for most nuclei across the tissue section, the expected result of a probe against the Alu satellite sequence. The reactions containing the hybridization buffer with the 500,000 molecular weight dextran sulfate did not yield as strong a signal and the intensity was not the same for each cell nucleus. For these reactions, there were some slides in which regions of the tissue section stained very poorly and other regions that did not stain at all. Out of 10 slides hybridized with the 500 K dextran sulfate buffer, 8 of those slides had regions in the tissue sections which had weak nuclear signal and some regions which had no signal at all. Conversely, among the 10 slides hybridized with the low molecular weight dextran sulfate buffer of the present invention, only one of those slides had a region of the tissue section that exhibited poor staining. This observation of poor staining was deduced to be due to the uneven spreading and/or mixing of the hybridization buffer across the tissue section. For this experiment, that phenomena was common among the reactions based on the 500 K dextran sulfate buffer.

The hybridization reactions with cocktails made with the low molecular weight dextran sulfate routinely yielded a more intense signal with the Alu satellite sequence probe compared to the reactions with 500K dextran sulfate buffer. This observation suggests (1) that low molecular weight dextran sulfates are effective volume exclusion agent for hybridization reactions, and (2) and such buffers are more efficient than corresponding buffers made with 500K dextran sulfate for automated hybridization protocols.

Example 2

ISH on Human Spleen Samples

Figure 1B:
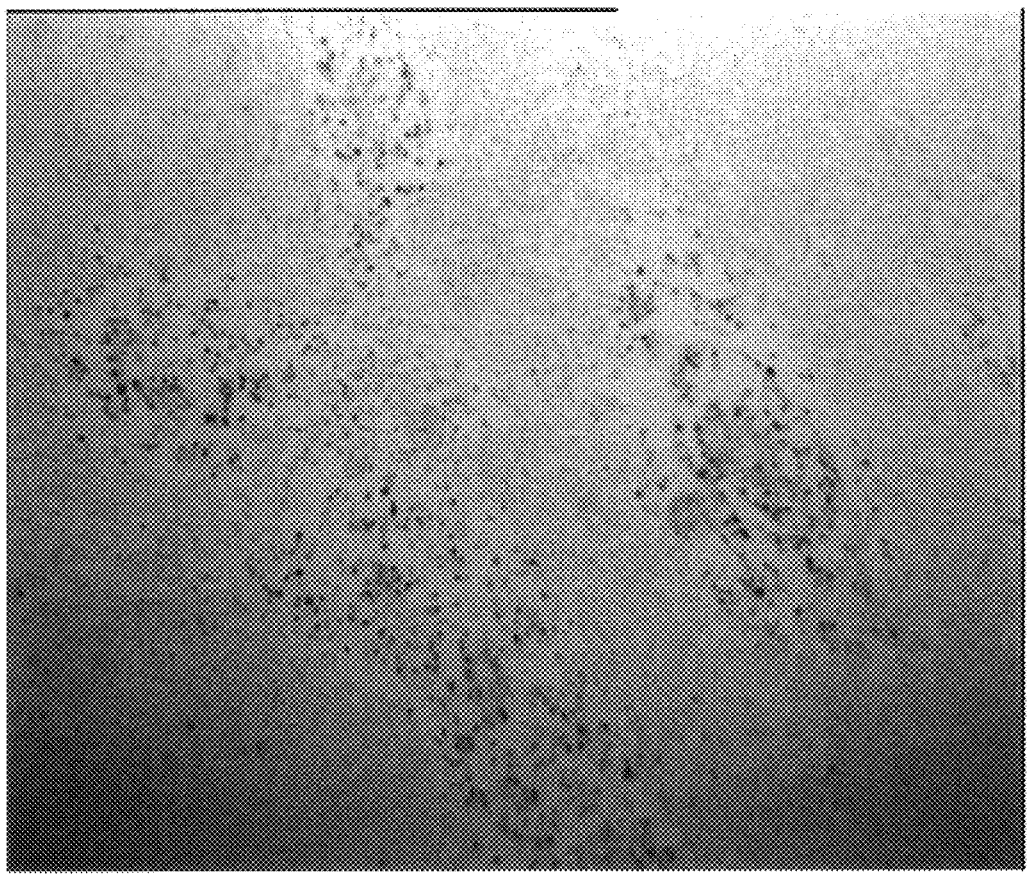

FIGS. 1A–1B illustrate the results obtained for ISH analysis of human spleen tissue using a probe collection consisting of labeled oligonucleotides that are complementary to the EBV early RNA transcripts, EBER 1 and 2. This experiment demonstrated that dextran sulfate hybridization buffers using 10,000 MW supports the specific hybridization between DNA oligonucleotide probes and RNA targets, in this case nuclear RNAs. These two viral transcripts are nuclear RNA. Target specificity is demonstrated by the loss of signal with tissues treated with RNase prior to hybridization (B) versus tissue sample not treated with ribonuclease A prior to in situ hybridization (A). The decrease in detectable signal in (B) indicates that this probe specifically hybridizes to RNA transcripts, EBER 1 and EBER 2.

Example 3

ISH on Lymphoma Tissue Samples

Figure 2A:
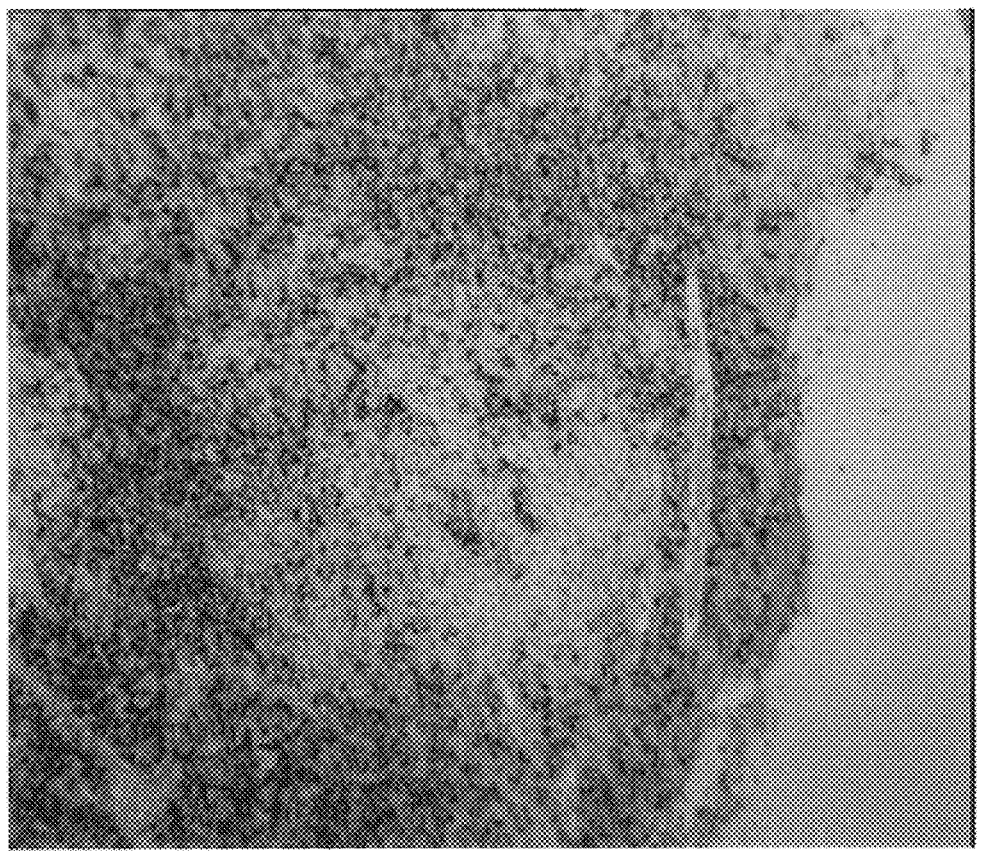
FIGS. 2A and 2B are color photographs of lymphoma tissues using a probe collection consisting of probes possessing target gene-specific domains corresponding to human immunoglobulin kappa light chain mRNA. The lymphoma tissue in FIG. 2A overexpresses the kappa light chain and the tissue in FIG. 2B overexpresses the lambda light chain.
Figure 2B:
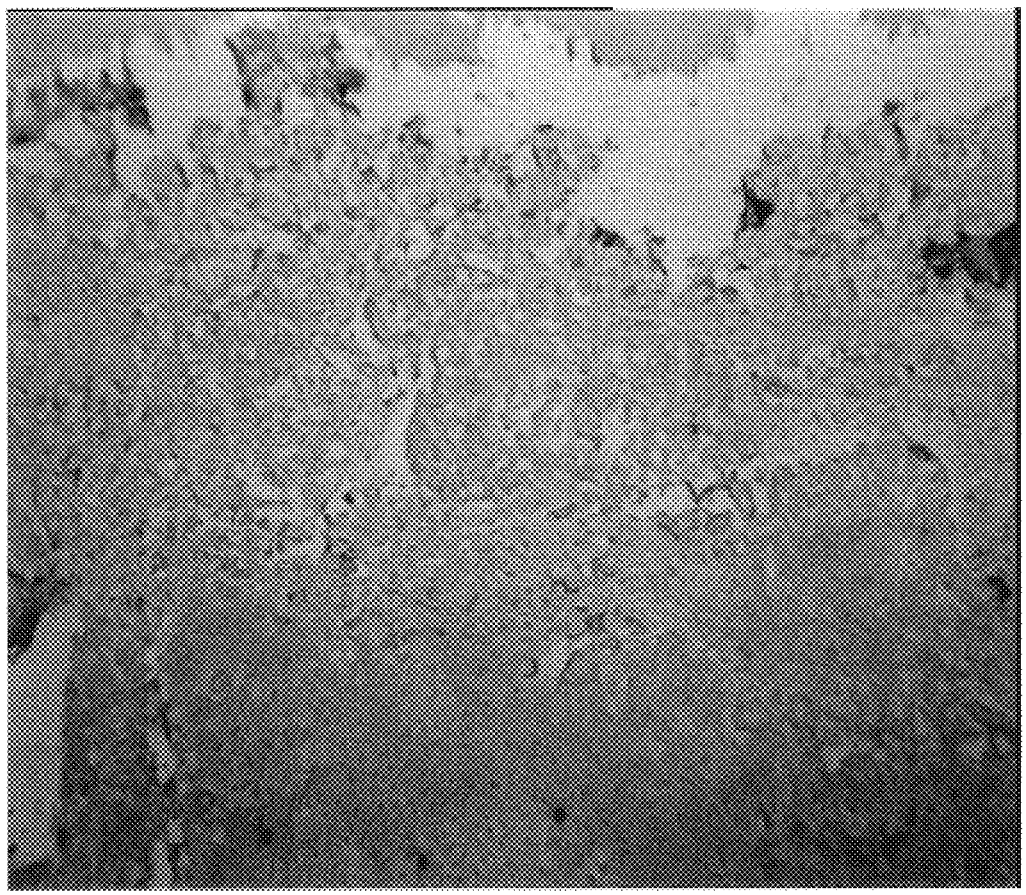
Figure 3A:
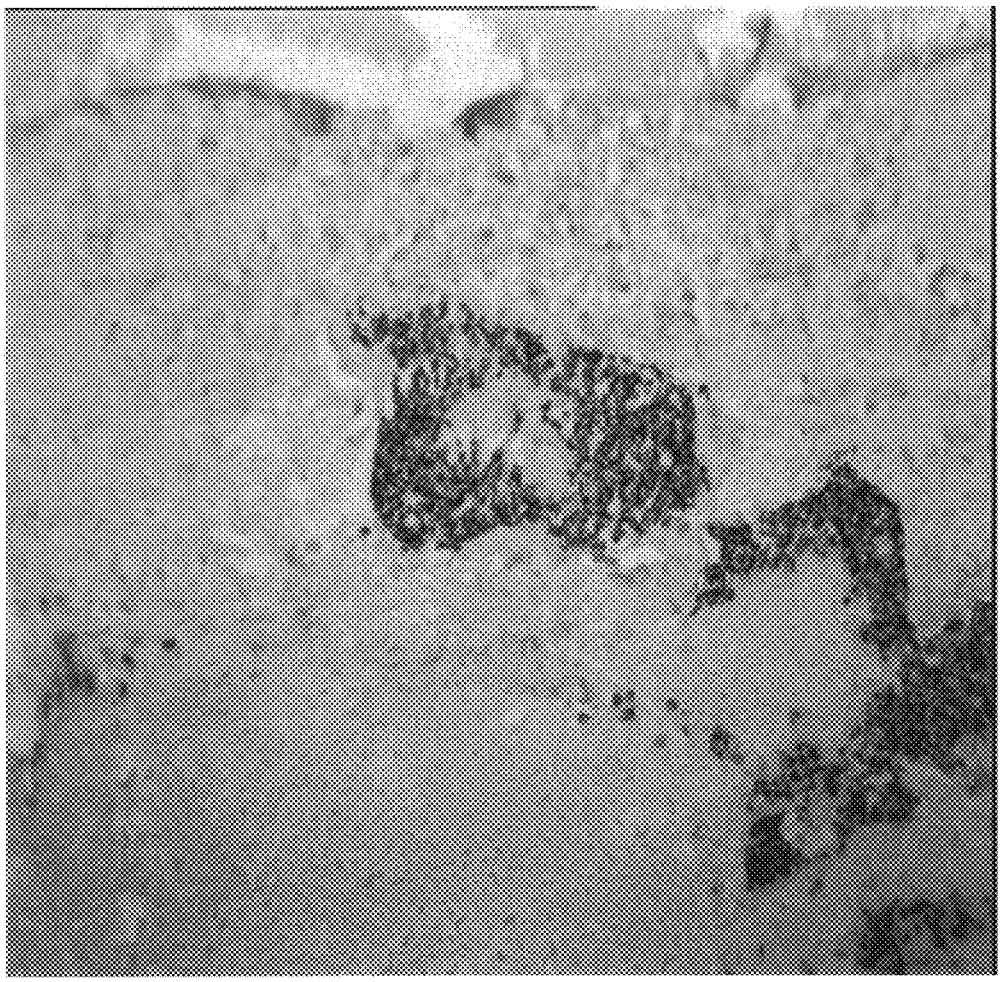
FIGS. 3A and 3B are color photographs of human lymphoma tissues using a probe collection consisting of probes possessing target gene-specific domains corresponding to human immunoglobulin lambda light chain mRNA. The tissue in FIG. 3A over expresses the lambda light chain and the tissue in FIG. 3B over expresses the kappa light chain.
Figure 3B:
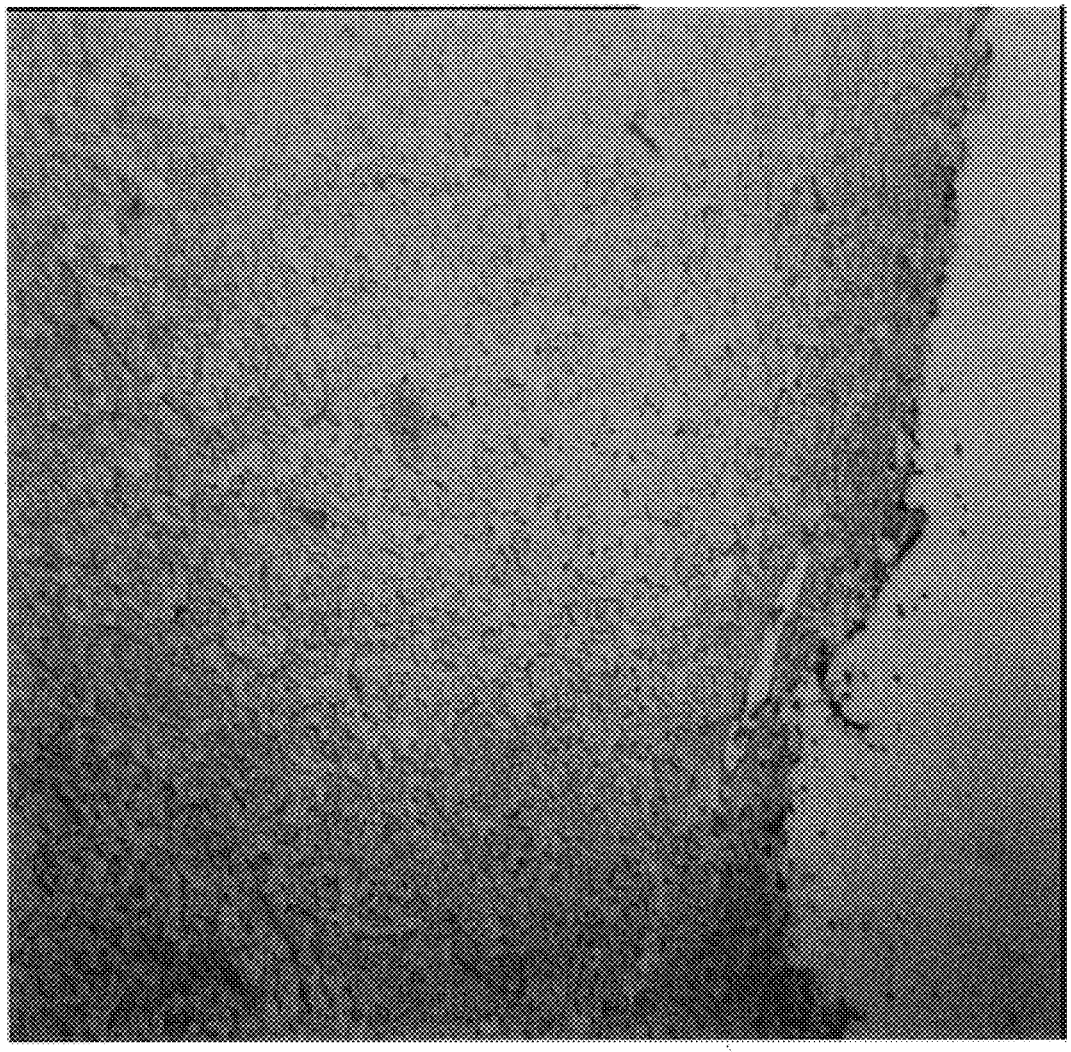

FIGS. 2 and 3 illustrate that the hybridization buffers with low molecular weight dextran sulfate support specific hybridization reactions by a comparison of two probe collections, each specific to mRNA of the two human immunoglobulin light chain genes, kappa and lambda respectively. The tissues used were plasmacytoid lymphoma tissues each being monoclonal in origin for one or the other light chain mRNA. In FIG. 2A, the tumor was kappa monoclonal as shown by the abnormally high frequency kappa expressing cells, whereas the tissue in FIG. 2B was a tissue monoclonal for lambda gene expression, thus a low level of kappa expressing cells were found. The reverse was found in the tissue in FIG. 3. Using a lambda probe this monoclonality was discerned as illustrated in FIGS. 3A and 3B. The tissue in FIG. 3A shows a high frequency of cells that are over expressing lambda light chain mRNA; tissue in FIG. 3B had a low frequency of lambda expressing cells. Thus for probes from related genes, the low molecular weight dextran sulfate buffer can support specific hybridization.

Example 4

ISH Using Buffer B

Figure 4:
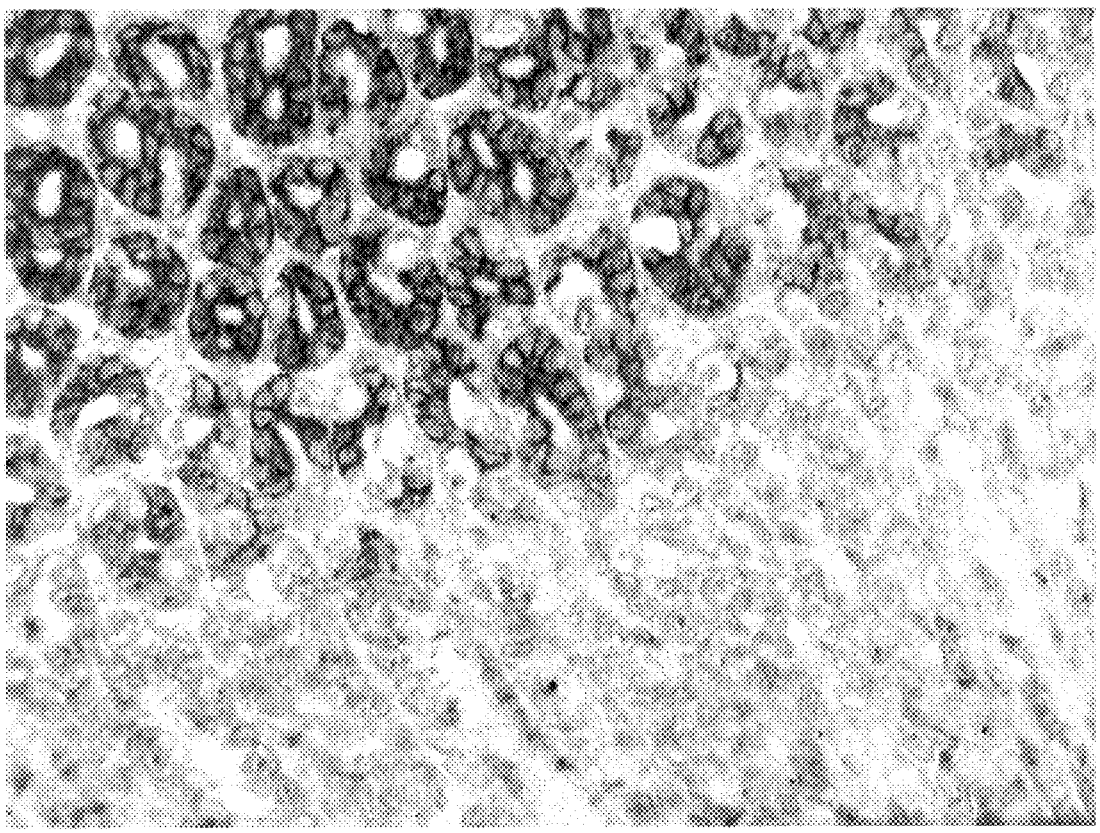
FIG. 4 is a color photograph of a slide-based in situ hybridization image of mouse pS2 gene expression in the mouse stomach using mouse pS2 antisense riboprobe diluted in Buffer B.

FIG. 4 is a color photograph of a slide-based in situ hybridization image of mouse pS2 gene expression in the mouse stomach using mouse pS2 antisense riboprobe diluted in Buffer B. The mouse mPS2 gene, found to be expressed in normal stomach epithelium (Lefebvre, O., Wolf, C., Kédinger, M., Chenard, M. P., Tomasetto, C., Chambon, P., Rio, M. C., "The mouse one P-Domain (pS2) and two P-Domain (mSP) genes exhibit distinct patterns of expression," *J. Cell Biol.*, 122:191–198 (1993)), was used as a model to study the use of the Buffer B hybridization buffer. The mPS2 cDNA was provided sub-cloned in a pBluescript plasmid (Promega, Madison), suitable and linearized for in vitro transcription.

Anti-sense and sense DIG-labeled riboprobes were synthetized using the Roche RNA DIG labeling kit (Roche Molecular cat# 1 175 025) and solubilized in a final volume of 200 μl H2O (stock solution). A 1:1000 dilution of the mPS2 riboprobes into the Buffer B buffer provided the working dilution.

Formalin-fixed, paraffin-embedded mouse stomach sections (5 μm) were hybridized on the DISCOVERY instrument platform, after on-line deparaffinization and digestion steps. Probe and slides were co-denatured at 70° C. for 6 minutes, and hybridized for 3 hours at 60° C. Hybridization was followed by three stringency washes of 6 minutes each, using 0.1× SSC at 65° C.

The probe was detected by immunohistochemistry using a biotinylated anti-Dig antibody (Sigma, 1:200), followed by a Streptavidin-Alkaline Phosphatase & NBT/BCIP colorimetric detection (Ventana Enhanced Blue detection kit).

Signal was found in the epithelial cells of the human stomach using the anti-sense probe, while no signal was detected using the sense probe. Localization of the signal was found to be appropriate by comparing with previously published radioactive ISH results (Lefebvre et al., 1993).

Example 5

ISH on HPV Control Cell Lines in Paraffin-embedded Tissue

Figure 9:
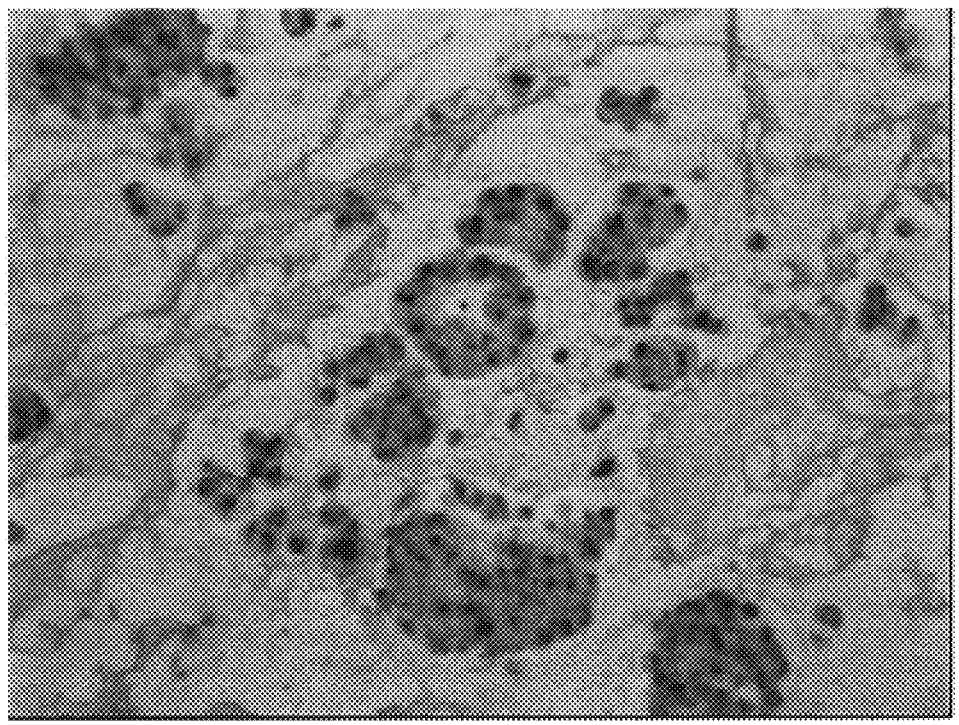
FIG. 9 is a color photograph of paraffin-embedded cell lines of Caski cells, having approximately 500 copies of HPV 16 integrated into the cellular nuclei.
Figure 10:
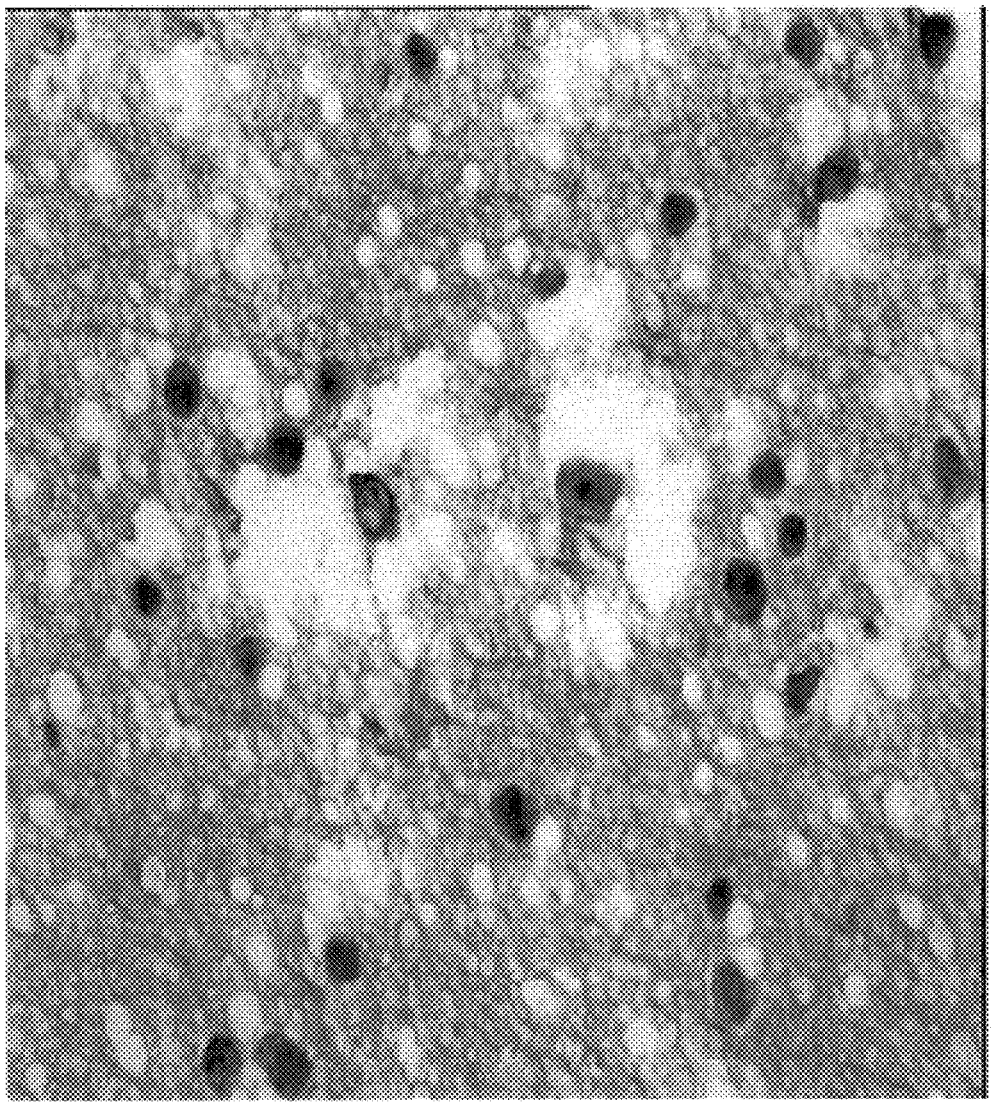
FIG. 10 is a color photograph of paraffin-embedded control cell lines of HeLa cells, having approximately 20–50 copies of HPV 18 integrated into the cellular nuclei.

For ISH using HPV probes as a cocktail of cloned DNAs of HPV high-risk or low-risk strains (described in co-owned international patent application PCT/US99/25109), hybridization reactions were carried out at stringencies which allowed discernment between high-risk and low-risk strains of HPV in paraffin-embedded tissues. The hybridization reactions were carried out at 57 degrees C. for 2 hours followed by 2× SSC washes at 76° C. The final concentration of hybridization buffer components were 25% formamide (vol/vol), 2× SSC, 5 mM Tris, 2.5 mM EDTA, 0.025% Brij-35, 0.25% Triton X-100 at 0.25% wt vol. The samples were paraffin embedded cell lines of (a) Caski (approximately 500 copies of HPV 16) (FIG. 9) and (b) HeLa cells with HPV 18 (copy number within a range of 20 to 50 per cell) (FIG. 10). The diseased tissues were paraffin-embedded cervical tissues infected with HPV.

The results were as follows. FIG. 9 shows that the Caski paraffin-embedded cell lines have good signal in the expected nuclear pattern with low to no background on the nuclei. FIG. 10 shows that HeLa embedded cells have a smaller nuclear signal spot, as expected from the lower copy number with low to no background.

A proprietary Her-2/neu gene (c-erbB2) DNA probe was tested using Buffer A as the volume exclusion agent. The probe was tested in this buffer using paraffin-embedded cell line slides (Ventana Medical Systems, Inc. cat. no. S8100) and breast carcinoma tissues. The embedded cell line kit consists of slides each having a cell line which has different copy numbers of Her-2/neu gene: the level 1 slides (Oncor catalogue number s8100-1) have cells with the normal copy number of Her-2/neu gene (3 or less); the level 2 slides (Oncor catalogue number s8100-2) have cells with the low amplified level of Her-2/neu gene, 4 to 10 copies; the level 3 slide (Oncor catalogue number s8100-3) cells have highly amplified numbers of the Her-2/neu gene, 10 copies or more. The slides were processed on the DISCOVERY instrument. The slides were deparaffinized online, pretreated with a detergent solution at 90C. then further treated with Ventana Protease 1 (catalogue number 760-2018) for 4 minutes at 37° C. for embedded cells and 10 minutes at 50° C. for embedded tissue. The denaturation was performed at 90° C. for 10 minutes and hybridization was for 12 hours at 50° C. Post-hybridization washes were 6 minutes at 50° C. in 2× SSC followed by 6 minutes at 60° C. in 2× SSC. Hybrids were detected by indirect fluorescence detection by binding a FITC-labeled anti-Biotin antibody followed by FITC-labeled anti-Mouse antibody. Slides were counterstained with propidium iodide and coverslipped after the finish of the automated processing.

Figure 6:
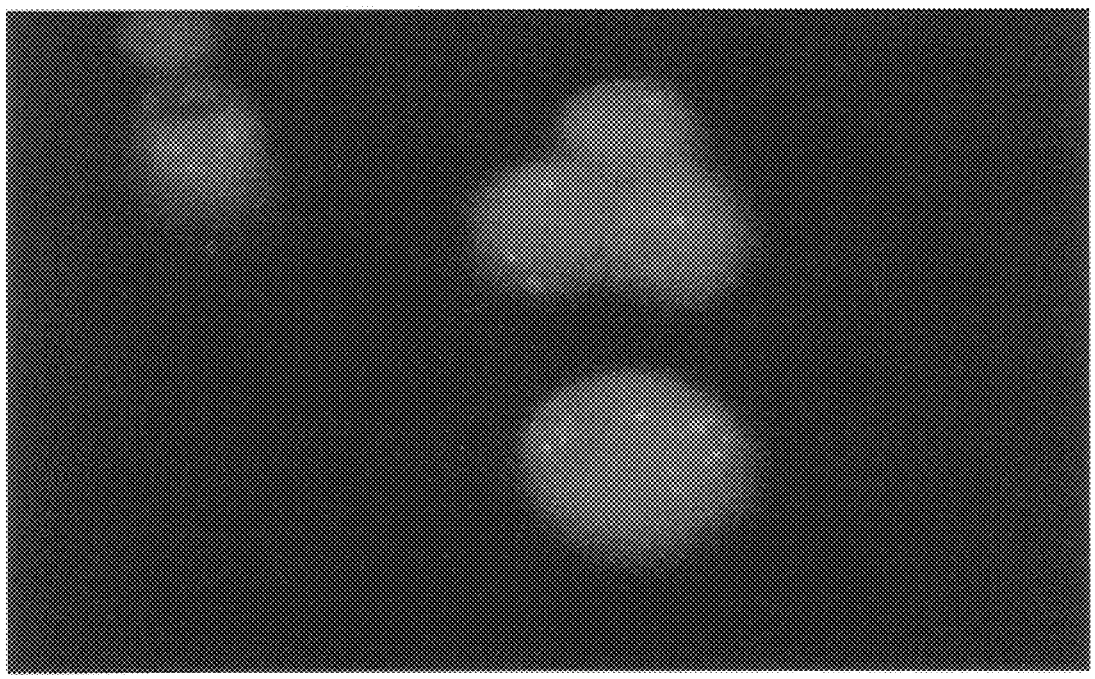
FIG. 6 is a color photograph of a slide having the Her-2/neu hi-amplification control cell line, (Ventana Cat. No. S1003) hybridized to a Her-2/neu DNA probe.
Figure 7:
FIG. 7 is a color photograph of a slide having the Her-2/neu low-amplification control cell line, (Ventana Cat. No. S1002) hybridized to the same Her-2/neu DNA probe.
Figure 8:
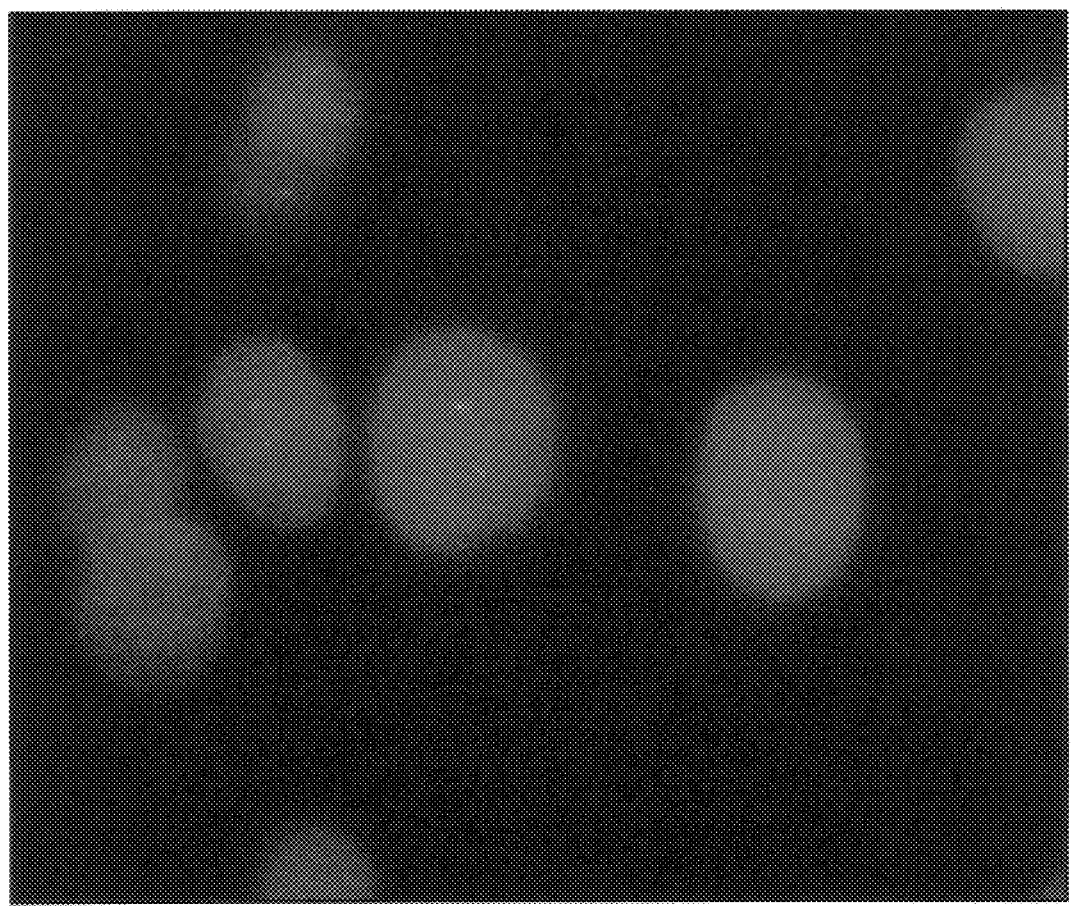
FIG. 8 is a color photograph of a slide having the Her-2/neu non-amplified control cell line, (Ventana Cat. No. S1001) hybridized to a Her-2/neu DNA probe.

The results were as follows. With reference to FIGS. 6–8, the embedded cell lines have strong signal of the expected pattern with low to no background on the nuclei. The tissue has signal on the tumor cells with a low level of background. Thus, the hybridization buffer with 10% dextran sufate of 10,000 MW allows controlled hybridization stringency and good results with Her-2/neu probes using a 12 hour hybridization performed under LIQUID COVERSLIP™, on both control cell lines and patient tissue specimens. FIG. 6 illustrates signal from for high-amplification of the Her-2/neu gene (greater than 10 copies/cell). FIG. 7 illustrates signal from low-amplification of the her-2/neu gene (greater than 4, but less than 10, copies/cell). FIG. 8 illustrates signal from diploid copy number Her-2/neu gene.

Example 6

In vivo ISH Hybridization Using Buffer C

Figure 5:
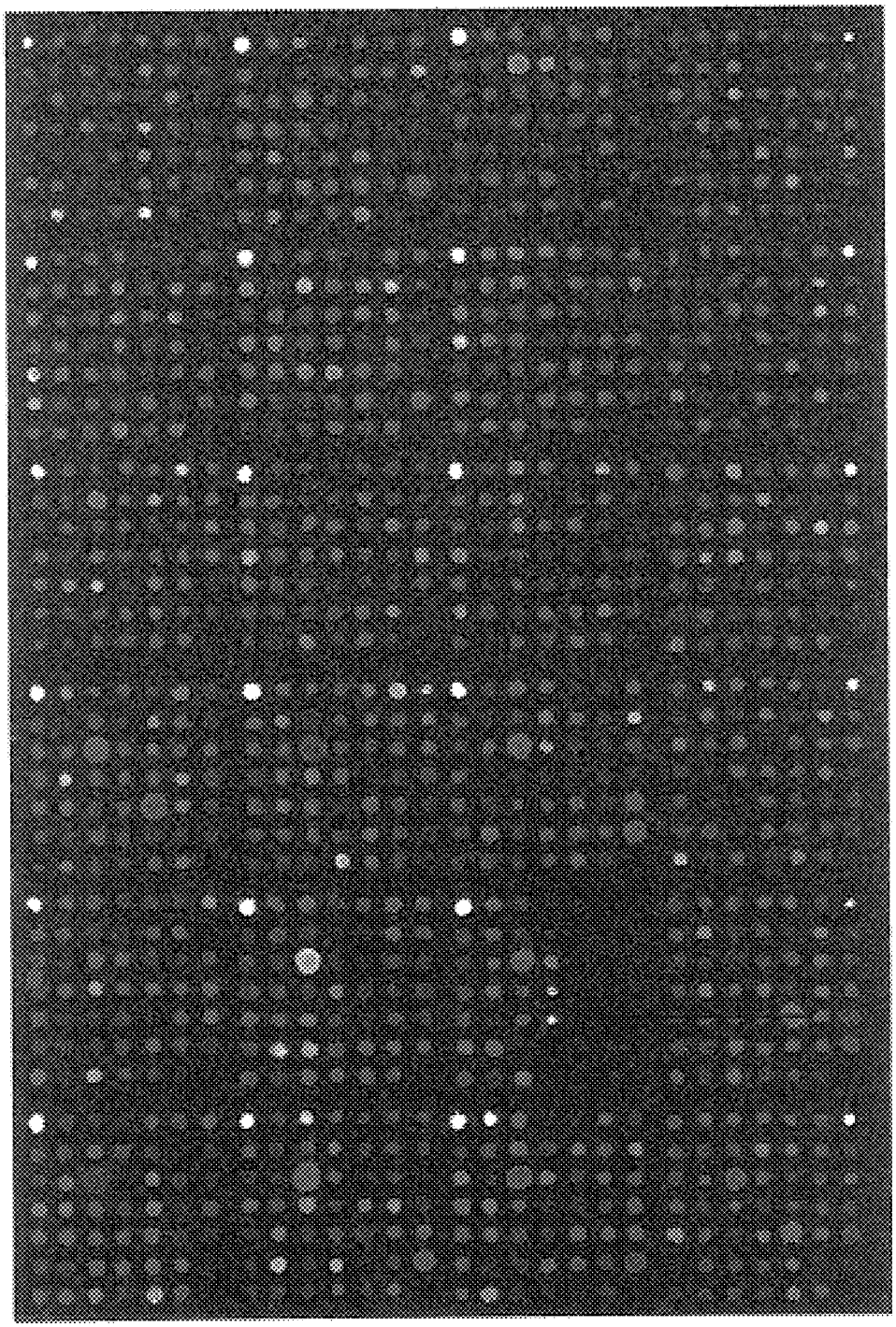
FIG. 5 is a scanned color photograph of the ClonTech Human Atlas DNA microarray probed with Cy3-labelled amplified cDNA probe from placental RNA.

FIG. 5 is a color photograph of a ClonTech Human Atlas DNA microarray (ClonTech, Inc., Palo Alto, Calif.) that was probed using Cy3-labelled amplified cDNA probe from placental RNA (Ambion, Austin, Tex., Cat# 7950). The probes were labeled according to the method of Zhao, R., Gish, K., Murphy, M., Yin, Y., Notterman, D., Hoffmnan, W. H., Tom, E., Mack, D. H. and Levine, A. J., "Analysis of p53-regulated gene expression patterns using oligonucleotide arrays," Genes & Development 14: 981–983 (2000). Hybridization Buffer C was used to hybridize the probes to the DNA microarray oligonucleotides using standard instrument protocols.

It should be understood that the foregoing disclosure emphasizes certain specific embodiments of the invention and that all modifications or alternatives equivalent thereto are within the spirit and scope of the invention as set forth in the following appended claims. All patents, patent applications, and references cited herein are incorporated by reference.

We claim:

1. In an automated tissue staining system having evaporation inhibitor liquid covering the polynucleotide hybridization buffer-covered tissue on a slide, wherein the improvement comprises a polynucleotide hybridization buffer for in situ hybridization comprising a low molecular weight dextran sulfate having a molecular weight range from about 8,000 to about 16,000.

2. The polynucleotide hybridization buffer of claim 1 wherein said dextran sulfate has a average molecular weight of about 13,000.

3. The polynucleotide hybridization buffer of claim 1 wherein the concentration of low molecular weight dextran sulfate ranges from about 5% to about 25%, wt./vol.

4. The polynucleotide hybridization buffer of claim 1 wherein said buffer optionally contains formamide having a concentration of from about 5% to about 80%, wt./vol.

* * * * *

UNITED STATES PATENT AND TRADEMARK OFFICE
CERTIFICATE OF CORRECTION

PATENT NO. : 6,656,685 B2
DATED : March 20, 2001
INVENTOR(S) : Hammond et al.

It is certified that error appears in the above-identified patent and that said Letters Patent is hereby corrected as shown below:

Column 6,
Line 6, delete "arid" and replace with -- and --.

Signed and Sealed this

Thirty-first Day of May, 2005

JON W. DUDAS
*Director of the United States Patent and Trademark Office*